United States Patent [19]

Schafer

[11] Patent Number: 5,014,686

[45] Date of Patent: May 14, 1991

[54] PHANTOM KIDNEY STONE SYSTEM

[75] Inventor: Mark E. Schafer, Blue Bell, Pa.

[73] Assignee: International Sonic Technologies, Horsham, Pa.

[21] Appl. No.: 401,625

[22] Filed: Aug. 31, 1989

[51] Int. Cl.[5] ............................................. A61B 17/22
[52] U.S. Cl. ................................................ 128/24 EL
[58] Field of Search ....................... 128/24 EL, 660.03; 606/127-128

[56] References Cited

U.S. PATENT DOCUMENTS

| | | |
|---|---|---|
| 3,310,885 | 3/1967 | Alderson . |
| 3,529,363 | 9/1970 | Versaci . |
| 4,493,653 | 1/1985 | Robins et al. . |
| 4,669,483 | 6/1987 | Hepp et al. ...................... 128/660.03 |
| 4,705,026 | 10/1987 | Chaussy et al. ................. 128/24 EL |
| 4,741,008 | 4/1988 | Franke . |
| 4,805,622 | 2/1989 | Riedlinger et al. . |
| 4,846,196 | 7/1989 | Wiksell et al. ....................... 128/784 |

OTHER PUBLICATIONS

Chaussy et al., *Extracorporeal Shock Wave Lithotripsy;* Karger, p. 22 (1982).

Primary Examiner—Lee S. Cohen
Assistant Examiner—John D. Zele
Attorney, Agent, or Firm—Arent, Fox, Kintner, Plotkin & Kahn

[57] ABSTRACT

The phantom kidney stone system for use with a commercial lithotripsy system includes a phantom kidney stone which simulates a human kidney stone and is suspended into the field of operation of the commerical lithotripsy system. The system also includes a trigger which is connected to receive a shock wave signal from the lithotripter which is representative of a shock wave output from the lithotripter. The trigger generates a trigger signal in response to the signal from the lithotripter. A counter is connected to receive the trigger signal and counts the number of trigger signals which is representative of the number of shock waves output from the lithotripter. A detection circuit is connected to the phantom kidney stone and produces a signal proportional to the detected size of the stone at a given point in time and compares the detected size of the stone to a predetermined reference size indicative of a condition wherein the stone would be crushed. The detection circuit generates an output signal at a time when the detected size of the stone is less than the reference size. A processor is connected to receive the output signal from the detection circuit and is connected to the counter and outputs the number of trigger signals which were counted by the counter at a time when the detection circuit generates the output signal. A display indicated the number to the user of the lithotripter.

20 Claims, 3 Drawing Sheets

PHANTOM KIDNEY STONE SYSTEM

BACKGROUND OF THE INVENTION

The present invention relates to a phantom kidney stone system for use with a commercial lithotripsy system.

Currently there is no uniformly repeatable test procedure which can be used by manufacturers and/or users of commercial lithotripsy systems for quality control purposes in order to ascertain that the lithotripsy system is functioning properly.

Also, there is no uniformly repeatable test procedure which can be used to train operators of commercial lithotripsy systems to improve the accuracy with which the operators perform an actual lithotripsy operation. There is a need for the operators to be trained properly so that when an actual lithotripsy operation is performed, the lowest possible number of shock waves are used to break up the kidney stone. It is necessary to keep the number of shock waves which are input into human tissue as low as possible. Therefore, operators should be trained prior to performing an actual lithotripsy operation on a human patient. At the present time, the operators do not have an opportunity to work with the lithotripsy system until they actually use the equipment on a human patient.

There is a further need to be able to accurately record the number of shock waves output by a lithotripsy system that are needed to break up a kidney stone into fragments of a size small enough to be excreted through the human urinary tract.

SUMMARY OF THE INVENTION

It is therefore an object of the present invention to provide a uniformly repeatable test procedure which can be used by manufacturers and/or users of commercial lithotripsy systems for quality control purposes in order to ascertain that the lithotripsy system is functioning properly.

It is a further object of the invention to provide a uniformly repeatable test procedure which can be used to train operators of a lithotripsy system.

Another object of the invention is to provide a system which accurately records the number of shock waves output by a lithotripsy system which are needed to break up a kidney stone.

Additional objects and advantages of the invention will be set forth in part in the description which follows, and in part will be obvious from the description, or may be learned by practice of the invention. The objects and advantages of the invention may be realized and attained by means of the instrumentalities and combinations pointed out in the appended claims.

To achieve the objects and in accordance with the purpose of the invention, as embodied and broadly described herein, this invention, in one aspect, includes a phantom kidney stone system for use with a commercial lithotripsy system having a field of operation and outputting shock waves to crush a kidney stone, the shock waves being output within the field of operation, each shock wave breaking up the stone into a plurality of fragments of a certain size, a number of the shock waves being necessary to break the stone up to a point where the stone is a stone crushed condition, the stone crushed condition indicating that the fragments are of a predetermined size small enough to be excreted through a human urinary tract.

The system includes phantom kidney stone means for simulating a human kidney stone, the stone means being suspended into the field of operation of the commercial lithotripsy system; trigger means, connected to receive a shock wave signal from the commercial lithotripsy system, the shock wave signal representative of a shock wave output from the commercial lithotripsy system, for generating a trigger signal in response to the signal from the commercial lithotripsy system; counting means, connected to receive the trigger signal, for counting the number of trigger signals representative of the number of shock waves output from the commercial lithotripsy system; detection means, connected to the phantom kidney stone means, for producing a signal proportional to a detected size of the stone means at a given point of time and for comparing the detected size of the stone means to a predetermined reference size, the reference size being indicative of a stone crushed condition, the detection means generating an output signal at a time when the detected size of the stone means is less than the reference size; processing means, connected to receive the output signal from the detection means and connected to the counting means, for outputting the number of trigger signals counted by the counting means at a time when the detection means generates the output signal; display means, connected to the processing means, for indicating to a user of the commercial lithotripsy system the number of shock waves output by the commercial lithotripsy system to reach the stone crushed condition.

The accompanying drawings, which are incorporated in and constitute a part of this specification, illustrate two embodiments of the invention and, together with the description, serve to explain the principles of the invention.

DESCRIPTION OF THE PREFERRED EMBODIMENT

Figure 1:
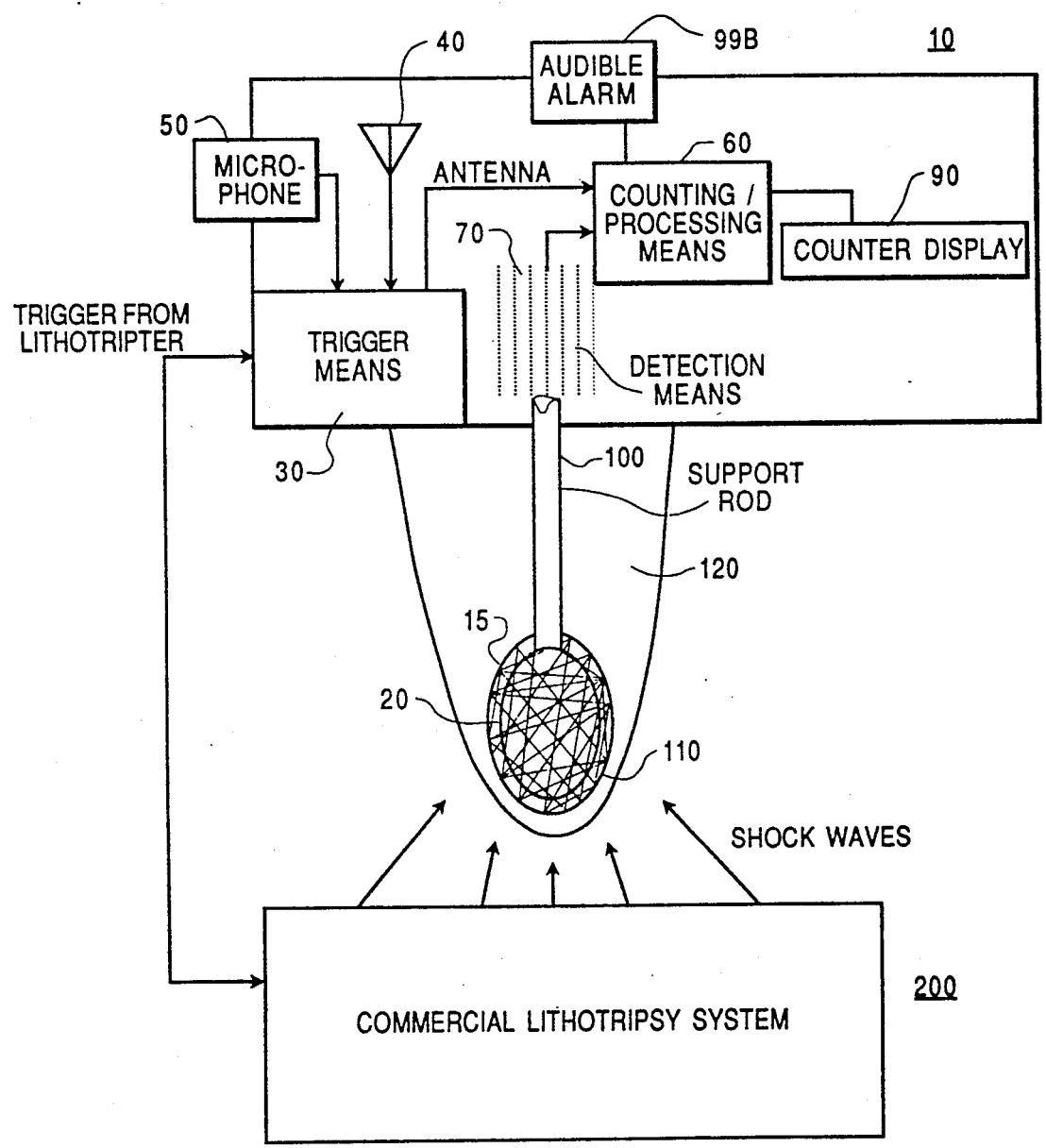
FIG. 1 is a block diagram illustrating a phantom kidney stone system for use with a commercial lithotripsy system in accordance with a preferred embodiment of the present invention.

Reference will now be made in detail to the present preferred embodiments of the invention, examples of which are illustrated in the accompanying drawings in which like reference characters refer to corresponding elements.

Figure 2:
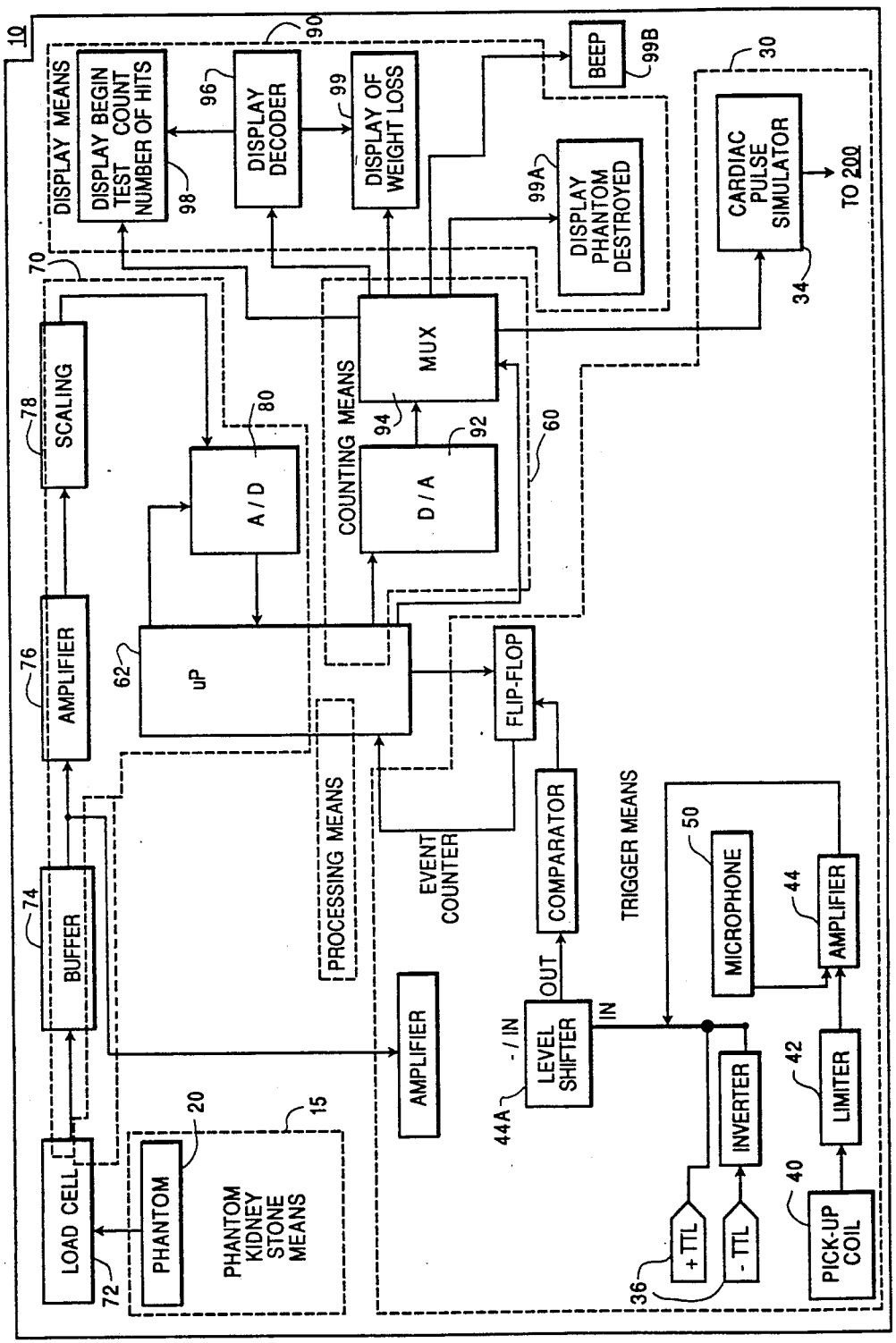
FIG. 2 is a more detailed block diagram illustrating the phantom kidney stone system of FIG. 1 in accordance with a first embodiment of the present invention.
Figure 3:
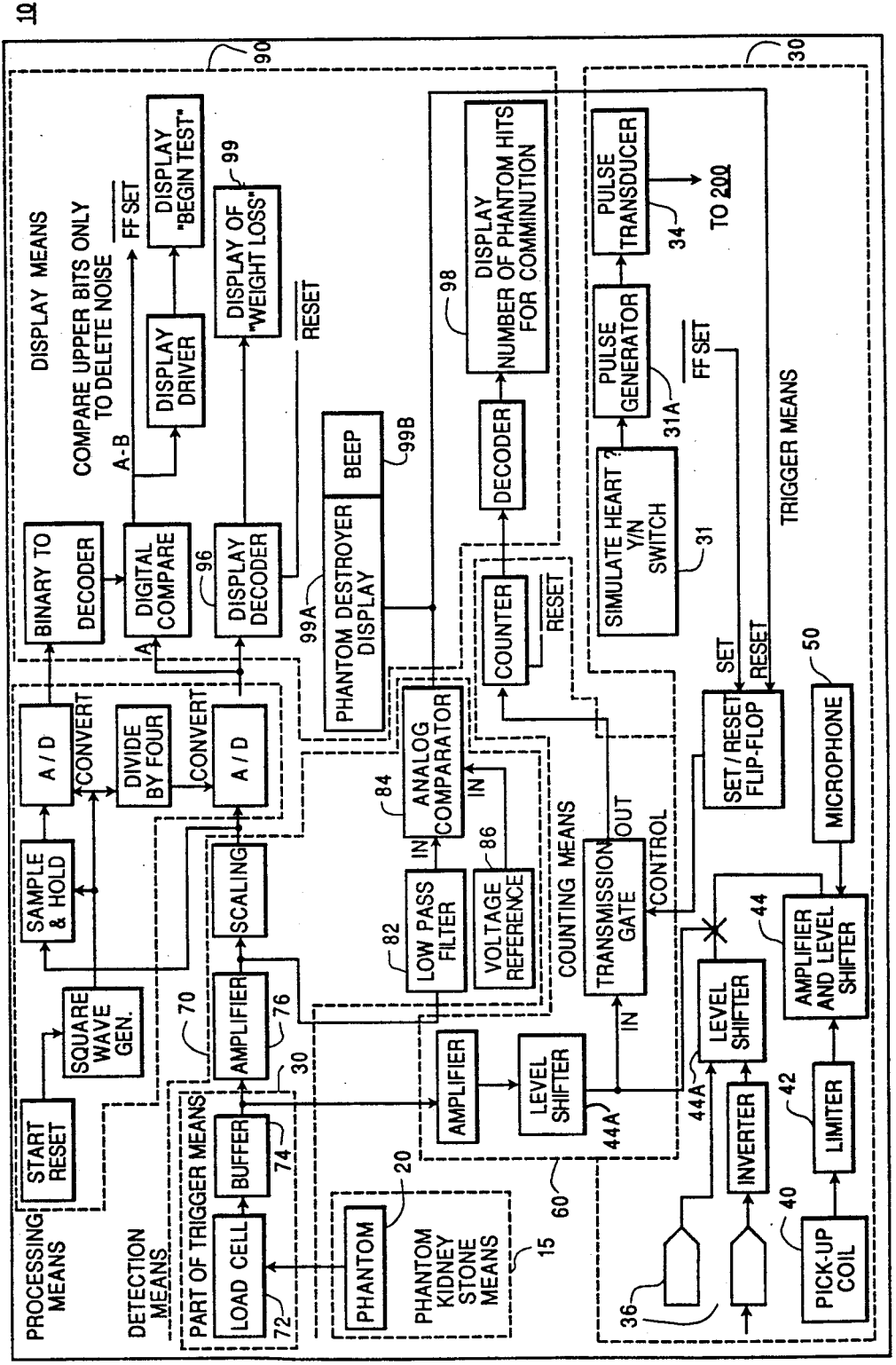
FIG. 3 is a more detailed block diagram illustrating the phantom kidney stone system of FIG. 1 in accordance with a second embodiment of the present invention.

Referring to FIGS. 1-3, the phantom kidney stone system constructed in accordance with the principles of the present invention is shown and is represented generally by the numeral 10. The phantom kidney stone system 10 is used with a commercial lithotripsy system 200. The commercial lithotripsy system 200 has a field of operation in which shock waves are output. The shock waves are used to crush kidney stones. A number of shock waves are output in order to break a kidney stone up to a point where fragments of the stone are of a predetermined size small enough to be excreted through a human urinary tract, generally less than 1 mm in diameter, which will be referred to as a "stone crushed" condition.

As shown in FIGS. 1-3, the phantom kidney stone system 10 includes phantom kidney stone means 15 for simulating a human kidney stone. As embodied herein, the phantom kidney stone means 15 includes a phantom stone 20 which is suspended into the field of operation of the commercial lithotripsy system 200. The material used to make the phantom stone 20 should mimic the characteristics of a human kidney stone. Typically, the stone 20 should be approximately 1 cm in diameter, a size which is an average size of a human kidney stone. A number of commercially available materials may be used to make the stone 20. For example, the stone 20 may be made from ($CaSO_4 \cdot \frac{1}{2}H_2O$). Also, a commercial material is available from High Medical Technologies of Oberaach, Germany which has been designed to mimic human kidney stones. It is important that the stone 20 be of a uniformly reproducible size and chemical composition.

The phantom kidney stone system 10 further includes trigger means 30 to receive a shock wave signal, the shock wave signal being representative of a shock wave output from the commercial lithotripsy system 200, for generating a trigger signal in response to the signal from the commercial lithotripsy system. As embodied herein, this trigger means 30 may include up to four types of triggers, the type of trigger to be used will be selected depending on the type of commercial lithotripsy system 200 which is being used in conjunction with the system 10 of the present invention.

For example, as shown in FIG. 2, some types of commercial lithotripsy systems 200 require an ECG pulse to set off a shock wave so that the shock waves are output in between cardiac pulses. Therefore, trigger means 30 is provided with an ECG simulator circuit, similar to the commercially available product Model M311 manufactured by FOG Systems Co., Inc. of Denver, Colo., which simulates a cardiac pulse to trigger the next shock wave of the commercial lithotripsy system 200. In this instance, system 10 is determining when a shock wave will be output by system 200.

Alternatively, as shown in FIG. 3, a switch 31 is provided wherein the operator is required to determine whether the particular lithotripsy system 200 requires a simulated cardiac pulse input. If so, the switch 31 is closed. When switch 31 is closed, ECG pulse generator 31A is turned on and outputs a simulated cardiac pulse to system 200.

For lithotripsy systems 200 which do not require a cardiac pulse or triggering in order to administer a shock wave, other means are provided within the trigger means 30 for determining when a shock wave has been output by system 200. Some types of commercial lithotripsy systems 200 have a built-in trigger signal output which can be input to TTL buffer 36 (TTL refers to transistor-transistor logic) of trigger means 30. For other types of commercial lithotripsy systems 200 which do not have a built-in trigger signal output, a coil antenna 40 can be used to pick up the electromagnetic interference signal that occurs during the shock wave output. The signal picked up by coil antenna 40 is output to limiter 42 which limits signal peak amplitude and outputs the signal to amplifier 44 which then amplifies the signal. The amplified signal is then used as a system trigger.

The third means for triggering included in trigger means 30 includes a microphone 50 which picks up the sound of the discharge after a shock wave is output by system 200. Amplifier 44 picks up the received signal and amplifies it. The amplified signal is filtered by level shifter 44A and is then detected.

The user of system 200 will select the type of triggering included in trigger means 30 depending on the type of system 200 by means of a switch. In order to confirm that system 10 is properly picking up trigger signals, a front-panel LED display may be provided which can flash for every detected shock wave output. Additionally, an audible signal may be used to "beep" indicating detection. This audible signal may be preferred in situations where users would prefer not to have to look at system 10 to confirm proper detection.

Additionally, the phantom kidney stone system 10 includes counting means 60, connected to receive the trigger signal, for counting the number of trigger signals representative of the number of shock waves output from the commercial lithotripsy system 200. As embodied herein, the counting means 60 includes a commercially available microprocessor 62, such as that known as 805X series and manufactured by Intel Corporation. The microprocessor 62 counts the trigger signals emitted from the trigger means 30 until the phantom stone 20 reaches the "stone crushed" condition.

The phantom kidney stone system 10 further includes detection means 70, connected to the phantom kidney stone 20, for producing a signal proportional to a detected size of the stone 20 at a given point of time and for comparing the detected size of the stone 20 to a predetermined reference size, the reference size being indicative of the stone crushed condition, the detection means 70 generating an output signal at a time when the detected size of the stone 20 is less than the reference size. As embodied herein, as shown in FIG. 2, the detection means 70 includes a load cell 72, such as that commercially available from Schaevitz Corporation. Because the weight of a typical intact stone 20 is only 2 grams, a high precision weighing mechanism is needed. The load cell 72 senses the weight of the stone 20. The load cell 72 outputs a DC electrical signal which is proportional to the weight of the stone 20. The signal from the load cell 72 is input to buffer 74 to convert impedance levels and/or filter the signal which is then input to amplifier 76 which amplifies the signal and to scaling circuit 78 to set the proper level of analog signal for A/D converter 80. Then the analog signal is converted to a digital signal by A/D converter 80. The digital signal is output by A/D converter 80 to microprocessor 62 which compares the digital signal to a value indicative of the weight of a stone upon reaching the "stone crushed" condition.

As shown in FIG. 3, the signal from load cell 72 may be input to buffer 74, then to amplifier 76 and then input to low pass filter 82 which removes high frequency noise from the signal. The signal from low pass filter 82 is input to analog comparator circuit 84 which compares the signal to a reference signal generated by voltage reference generator 86 indicative of the weight of a stone upon reaching the "stone crushed" condition. When the signal is less than the reference signal, the comparator outputs a signal indicating that the lithotripsy operation is completed.

Additionally, as an alternative to the use of the load cell 72, a fiber optic, chemical, ultrasound, capacitive or other detection means may be used to determine the size of the stone 20 at a given time.

The system 10 further includes processing means, connected to receive the output signal from the detection means 70 and connected to the counting means 60, for outputting the number of trigger signals counted by the counting means 60 at a time when the detection means 70 generates the output signal. As embodied herein, and as shown in more detail in FIG. 2, the processing means includes the microprocessor 62. The microprocessor 62 tracks the number of trigger signals counted by the counting means 60 and monitors the signal from A/D converter 80 until the "stone crushed" condition is met, at which time the microprocessor 62 generates a signal indicating that the lithotripsy operation is complete.

Additionally, the system 10 includes display means 90, connected to the microprocessor 62, for indicating to a user of the commercial lithotripsy system 200 the number of shock waves output by the commercial lithotripsy system 200 to reach the stone crushed condition. As shown in FIG. 2, the operation complete signal is output from microprocessor 62 to D/A converter 92 which converts the signal to an analog representation. The analog signal is then input to MUX 94 which is a n:l multiplexer (where n=6 in this embodiment), such as that commercially available from Analog Devices Corporation. MUX 94 allows microprocessor 62 to switch between several different outputs or displays. The analog signal is then sent to the display means 90. Display means 90 includes a display decoder 96 which decodes the signal and sends a signal to either a display count mechanism 98 which displays the number of trigger pulses counted by microprocessor 62, or to display weight mechanism 99. If the signal output by MUX 94 corresponds to a signal indicating that the "stone crushed" condition has been met, the signal will be output to unit 99A which displays an indication that stone 20 has been crushed. Additionally, the "stone crushed" signal is input to alarm 99B which sounds an audible alarm to indicate to the operator that the stone has been crushed and that the operation is complete. The unit 99A may simply display a yes/no indication. This type of display may be all that is necessary for quality assurance testing purposes. However, if system 10 is being used to train operators, display units 98 and 99 will be useful to give a continuous output of the weight of stone 20 and the number of shock waves which have been emitted from system 200.

The system 10 further includes suspension means 100 for connecting the stone 20 to the detection means 70. As embodied herein, the suspension means includes a support rod 100 as shown in FIG. 1 which may be comprised of any stiff material, preferably a material having a low acoustic impedance which is therefore less likely to reflect the energy of the shock waves emitted by the commercial lithotripsy system 200 and a material that is also transparent to X-rays, so that the image of the rod 100 does not interfere with the determination of the location of the stone 20 by the commercial lithotripsy system 200. In the preferred embodiment, polypropylene is used for the material for rod 100. Rod 100 may also include a number of notches at the end which is connected to detection means 70. The number of notches can be coded to indicate the initial weight of stone 20 or the type of commercial lithotripsy system 200 being tested or the length of rod 100.

The phantom kidney stone system 10 further comprises filter means 110, as shown in FIG. 1, for enclosing the phantom kidney stone means 15 and for keeping the fragments from breaking away until the stone reaches a stone crushed condition. The stone is crushed to a fine powder which can migrate across the filter means 110. As embodied herein, the filter means 110 is comprised of a plastic mesh material having a low acoustic impedance. The size of the mesh openings is predetermined to equal a size wherein the fragments of the stone 20 which pass through the mesh material are of the size small enough to be excreted through a human urinary tract. The filter means 110 is used so that during the output of shock waves, the fragments will not break away and interfere with the operation of system 200. The fragments cannot pass through the filter means 110 until they reach the stone crushed condition. Once this is completed, the lithotripsy operation is complete.

The system 10 further comprises membrane means 120, the membrane means 120 being filled with fluid, the phantom kidney stone means 15 being suspended in the membrane means 120, for guaranteeing uniformity in procedure and for preventing the fragments from breaking up and falling into the commercial lithotripsy system 200. As embodied herein, the membrane means 120 is made from Mylar and filled with polyethylene glycol or other acoustically-low impedance fluid.

As illustrated above, the system 10 provides a uniform and repeatable way to simulate a lithotripsy operation performed to break up a kidney stone. For quality assurance testing, a lithotripsy operation may be performed daily. A log can be kept indicating the number of shock waves needed for reaching the stone crushed condition. When the number begins to deviate, the user of the commercial lithotripsy system 200 will be alerted that the system 200 may need repairs or adjustments.

The system 10 may be used also to train operators. The operators may be trained using system 10 with system 200 before using the system 200 on a human patient. The operator will learn how to place the equipment so that the minimum number of shock waves are output by system 200 to reach the stone crushed condition. Additionally, other training techniques can involve using different sizes and thicknesses of the stone 20 to better simulate the variations in human kidney stones.

It will be apparent to those skilled in the art that various modifications and variations can be made in the apparatus of the present invention without departing from the scope or spirit of the invention. Thus, it is intended that the present invention cover the modifications and variations of this invention provided they come within the scope of the appended claims and their equivalents.

What is claimed is:

1. A phantom kidney stone system comprising:
   a commercial lithotripsy system having a field of operation and an ECG input and outputting shock waves to crush a kidney stone, said shock waves being output within said field of operation, each shock wave breaking up said stone into a plurality of fragments of a certain size, a number of shock waves being necessary to break said stone up to a point where said stone is in a stone crushed condition, said stone crushed condition indicating that said fragments are of a predetermined size small enough to be excreted through a human urinary tract;

phantom kidney stone means for simulating a human kidney stone, said stone means being suspended into the field of operation of said commercial lithotripsy system;

trigger means, connected to receive a plurality of shock wave signals from said commercial lithotripsy system, each of said shock wave signals being representative of a shock wave output from said commercial lithotripsy system, for generating a plurality of trigger signals, one of said trigger signals being generated in response to each of said shock wave signals from said commercial lithotripsy system;

counting means, connected to receive each of said trigger signals, for counting the number of trigger signals representative of the number of shock waves output from said commercial lithotripsy system;

detection means, connected to said phantom kidney stone means, for producing a signal proportional to a detected size of said stone means at a given point of time and for comparing the detected size of said stone means to a predetermined reference size, said reference size being indicative of the stone crushed condition, said detection means generating an output signal at a time when said detected size of said stone means is less than said reference size;

processing means, connected to receive said output signal from said detection means and connected to said counting means, for outputting the number of trigger signals counted by said counting means at a time when said detection means generates said output signal;

display means, connected to said processing means, for indicating the number of shock waves output by said commercial lithotripsy system to reach said stone crushed condition.

2. The phantom kidney stone system as claimed in claim 1, further comprising alarm means, connected to said processing means, for generating an audible alarm signal indicating said stone crushed condition.

3. The phantom kidney stone system as claimed in claim 1, further comprising suspension means for suspending said phantom kidney stone means into the field of operation of said commercial lithotripsy system.

4. The phantom kidney stone as claimed in claim 3 wherein said suspension means comprises a support rod made of a material having a low acoustic impedance.

5. The phantom kidney stone system as claimed in claim 4 wherein said support rod is comprised of a material which is transparent to x-rays.

6. The phantom kidney stone system as claimed in claim 5 wherein said support rod includes a number of notches at one end, said one end being connected to said detection means, said number of notches indicating the initial weight of said phantom kidney stone means.

7. The phantom kidney stone system as claimed in claim 5 wherein said support rod includes a number of notches at one end, said one end being connected to said detection means, said number of notches indicating the length of the support rod.

8. The phantom kidney stone system as claimed in claim 5 wherein said support rod includes a number of notches at one end, said one end being connected to said detection means, said number of notches indicating the type of commercial lithotripsy system being used.

9. The phantom kidney stone system as claimed in claim 1, further comprising filter means for enclosing said phantom kidney stone means and for keeping said fragments of a certain size from breaking away until said stone crushed condition has been met.

10. The phantom kidney stone system as claimed in claim 9 wherein said filter means is comprised of a plastic mesh material having a low acoustic impedance.

11. The phantom kidney stone system as claimed in claim 10 wherein the size of the mesh openings is predetermined to equal a size wherein said fragments of a certain size which pass through said mesh openings are of said size small enough to be excreted through a human urinary tract.

12. The phantom kidney stone system as claimed in claim 11 wherein the size of the mesh openings is less than 1 mm.

13. The phantom kidney stone system as claimed in claim 1, further comprising membrane means, said membrane means being filled with fluid, said phantom kidney stone means being suspended in said membrane means, for preventing said fragments from breaking up and falling into the commercial lithotripsy system.

14. The phantom kidney stone system as claimed in claim 1 wherein said phantom kidney stone means is comprised of a stone of $(CaSO_4 . \frac{1}{2} H_2O)$.

15. The phantom kidney stone system as claimed in claim 1 wherein said counting means comprises a microprocessor.

16. The phantom kidney stone system as claimed in claim 1 wherein said trigger means comprises:
a microphone, connected to receive said shock wave signal from said lithotripter;
an amplifier, connected to said microphone, said amplifier amplifying said received signal;
a filter, connected to said amplifier, filtering noise from said amplified received signal; and
trigger detection means, connected to said filter, for detecting said filtered amplified received signal and for generating said trigger signals.

17. The phantom kidney stone system as claimed in claim 1 wherein said trigger means receives:
a TTL trigger signal output generated by said lithotripsy system simultaneous with the output of said shock waves from said lithotripsy system; and further comprising:
a TTL buffer, connected to said lithotripter, buffering said TTL trigger signal output.

18. The phantom kidney stone system as claimed in claim 1 wherein the detection means includes a load cell, connected to said stone means, said load cell sensing the weight of said stone means and producing as an output a DC electrical signal proportional to the weight of said stone means.

19. The phantom kidney stone system as claimed in claim 16 wherein the detection means further includes a comparator circuit, said comparator circuit comparing said DC electrical signal to a reference signal indicative of said predetermined reference size and generating said output signal at said time when said detected size of said stone means is less than said predetermined reference size.

20. The phantom kidney stone system as claimed in claim 1 wherein said trigger means comprises:
an ECG pulse simulator means, connected to the ECG input to said commercial lithotripsy system, for generating trigger signals; and
control circuit means, connected to said ECG pulse simulator means, for setting a rate at which the commercial lithotripsy system is triggered.

* * * * *